United States Patent [19]

Parsons, Jr.

[11] 4,069,352

[45] Jan. 17, 1978

[54] IMMUNOADSORBENT POLYMERIC MATERIAL AND METHOD OF MAKING SAME

[75] Inventor: George H. Parsons, Jr., Arlington, Mass.

[73] Assignee: Baxter Travenol Laboratories, Inc., Deerfield, Ill.

[21] Appl. No.: 702,298

[22] Filed: July 2, 1976

[51] Int. Cl.² .................. G01N 33/16; G01T 1/16
[52] U.S. Cl. .................. 427/2; 23/230 B; 23/253 TP; 23/259; 195/103.5 A; 424/1; 424/12
[58] Field of Search ........... 23/230 B, 253 R, 253 TP, 23/259; 424/1, 12; 195/127, 103.5 A; 427/2

[56] References Cited

U.S. PATENT DOCUMENTS

| | | | |
|---|---|---|---|
| 3,646,346 | 2/1972 | Catt | 424/12 X |
| 3,826,619 | 7/1974 | Bratu, Jr. et al. | 424/12 X |
| 3,980,764 | 9/1976 | Adams | 424/1 |
| 3,995,019 | 11/1976 | Jerome | 424/12 X |
| 4,012,494 | 3/1977 | Ling | 424/12 X |

FOREIGN PATENT DOCUMENTS 1,257,263  12/1971  United Kingdom.

*Primary Examiner*—R.E. Serwin

[57] ABSTRACT

Gamma globulins from antisera having a titer so low in selected antibodies that the antibodies adsorbed on a surface of polymeric material are ineffective for use in immunoassay, are cross-linked, then adsorbed on the polymeric surface to provide an immunologically active coating. Binding proteins incapable of effective adsorption on polymeric surfaces are cross-linked with gamma globulin, then adsorbed on a surface of polymeric material capable of adsorbing gamma globulin to provide a specific binding protein coating. Kits containing test tubes having such coatings are used in radioimmunoassay, in enzyme immunoassay, and in fluoroimmunoassay.

21 Claims, 1 Drawing Figure

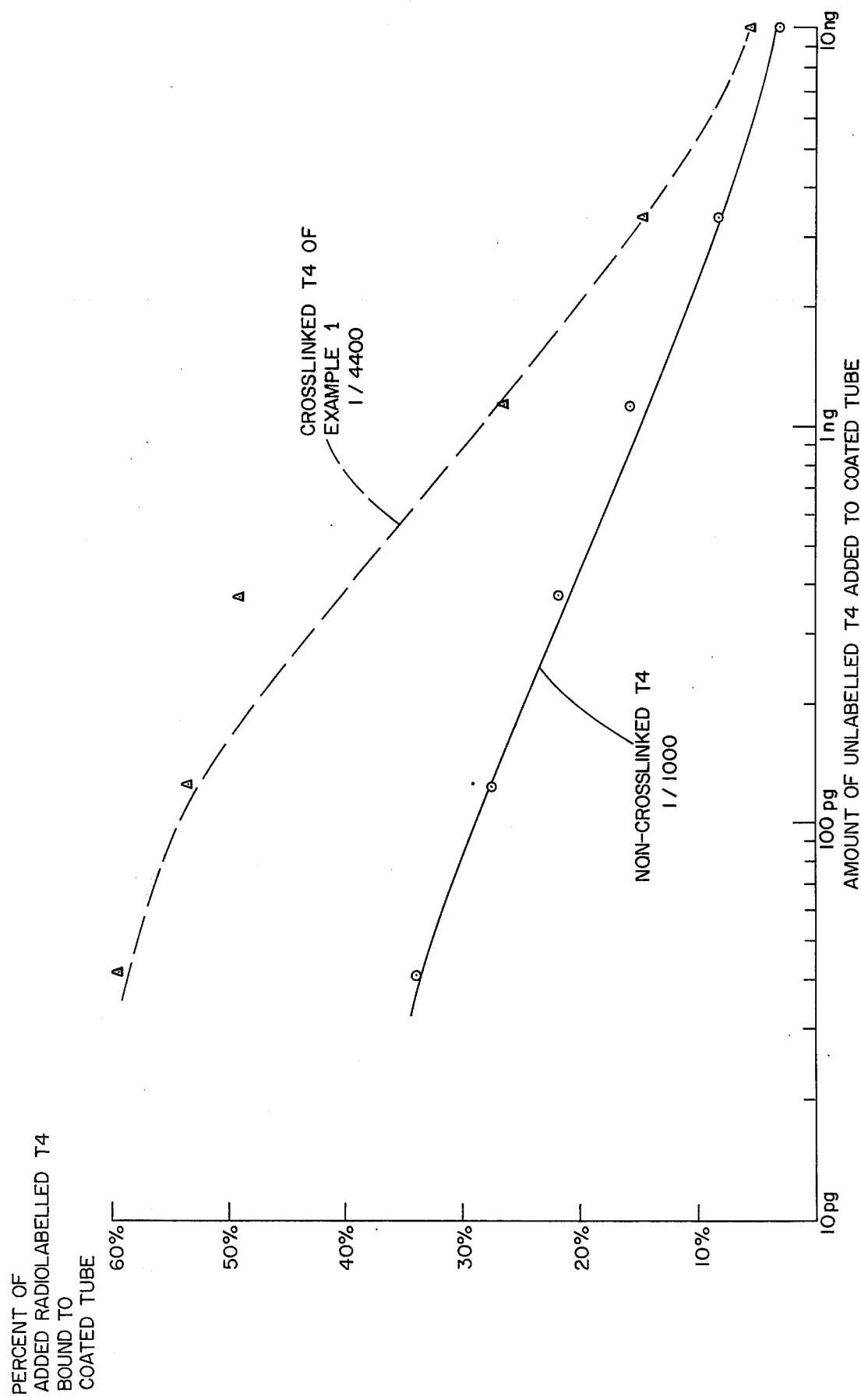

IMMUNOADSORBENT POLYMERIC MATERIAL AND METHOD OF MAKING SAME

This invention relates to immunoassay and competitive protein binding procedures and to a device for use in such procedures and pertains more specifically to a method and apparatus for radioimmunoassay, enzyme immunoassay, and fluoroimmunoassay of antigens.

It has previously been proposed in Catt U.S. Pat. No. 3,646,346 to provide a solid water-insoluble polymeric material, preferably in the form of a test tube, having its surface coated by adsorption of an antibody to the protein to be assayed, the coated tube then being brought into contact with an aqueous sample containing the protein to be assayed and also with a known quantity of the same protein which is radioactively labeled, finally separating the polymeric surface from the aqueous sample and determining, by measuring the emitted radiation, the amount of labeled protein which has been bound to the coated polymer. The solid phase antibody coated polymeric material can be made and used in the Catt procedure only when the antiserum containing the antibody to be adsorbed is of moderately high titer; moreover, the coated polymeric material and procedure cannot be used with some binding proteins such as hog gastric intrinsic factor (a binding protein for vitamin B-12) which are not adsorbed on polymeric surfaces sufficiently even when available in high titer solutions.

It has been proposed by Avrameas et al., Immunochemistry, Vol. 6, pages 53–66 (Pergamon Press, 1969) to insolubilize antigens or antibodies by cross-linking them with glutaraldehyde and to employ the insolubilized proteins thus produced, either in column procedure or in batchwise operation, for the isolation of antigens or antibodies. It has also been proposed by Avrameas, loc. cit., pages 43–52 to couple enzymes to human immunoglobulin-G and serum albumin as well as to sheep and rabbit antibody with glutaraldehyde and to use the products, which retain a substantial part of their immunological and enzymatic activity, for the intracellular detection of antigens and antibodies and for characterization of antibodies after immunoelectrophoresis. It has in addition been proposed by Barrett et al. at the Ninth International Congress on Clinical Chemistry, 13–18 July, 1975, Toronto, to bring a plastic tube into contact with glutaraldehyde to provide reaction aldehyde residues on the surface of the plastic, and then to bring the plastic into contact with antibody to cause the antibody to be coupled to the glutaraldehyde.

There has now been found a method of making a solid immunoadsorbent for use in immunoassay procedures which comprises cross-linking the gamma globulin content of low titer antiserum, bringing the cross-linked gamma globulin into contact with a surface of a solid polymeric material capable of adsorbing gamma globulin to form a coating of cross-linked gamma globulin adsorbed on said surface. There has further been found a method of making a solid immunoadsorbent for use in immunoassay procedures which comprises cross-linking a binding protein with gamma globulin to form a cross-linked material, then bringing the cross-linked material into contact with a surface of a solid polymeric material capable of adsorbing gamma globulin to form a coating of cross-linked material adsorbed on said surface. The solid polymeric material preferably is in the form of a plastic test tube as described in Catt et al. U.S. Pat. No. 3,646,346 having an inner surface of solid polymeric material capable of adsorbing gamma globulin, this adsorbed coating consisting essentially of cross-linked gamma globulin or of binding protein cross-linked to gamma globulin. The coated plastic tube is preferably supplied as part of a kit; the kit also contains a supply of labeled tracer and a standard, as described, for example, in Catt U.S. Pat. No. 3,646,346.

In the drawing,

The FIGURE is a graphical representation of the increase in binding capacity of a coated tube achieved by one embodiment of the present invention.

A kit such as that mentioned above is useful in both qualitative and quantitative immunoassay procedures for determining proteins, drugs, steroid hormones and other physiologically active materials which bind with their corresponding antibodies or binding proteins. The cross-linking step makes it possible to prepare useful solid immunoadsorbents from antisera of such low quality that they cannot be used effectively for adsorption of a selected antibody itself on the surface of polymeric material; the cross-linking step also makes it possible to prepare solid immunoadsorbents useful in immunoassay procedures from solutions of binding proteins which are incapable by themselves of sufficient adsorption on the polymeric surface, even from solutions of high titer, to prepare useful solid inmmunoadsorbents.

The amount or extent of cross-linking which is desirable varies depending upon the identity and concentration of the particular antiserum involved. In general, the extent of cross-linking desired for optimum results is from two to five times the molecular weight of the starting material. That is, the molecular weight of the cross-linked product is from two to five times the molecular weight of the uncross-linked antibody or binding protein. The time required for the desired extent of cross-linking may vary from a few minutes to several hours depending upon the identity of the proteins involved, and the nature of the cross-linking procedure employed. Cross-linking is generally carried out at a pH well below 8, whereas adsorption of the cross-linked product occurs to a substantial extent principally at a pH from 8 to 10, the optimum pH for adsorption depending upon the particular selected antibody or binding protein involved. Consequently, the cross-linking can be completed before bringing the antiserum or solution of binding protein into contact with the surface of the polymeric material, or if desired, the proteins can be cross-linked while in solution in contact with the surface of the solid polymeric material, after which the pH may be raised to pH 8–10 by addition of a suitable buffer to cause adsorption to occur without removing the solution from contact with the polymeric material.

Cross-linking can be effected by simple heating of the antiserum or of the mixture of binding protein with gamma globulin to a temperature of at least 55° C., preferably 70°–75° C. for a few minutes. Such heating causes cleavage of intramolecular disulfide linkages which occur in gamma globulins and frequently in binding proteins to generate reactive species which cross-link with each other.

Cross-linking can also be effectively carried out by mixing the antiserum or solution of binding protein and gamma globulin with sodium periodate, which causes cleavage of gem diols of those proteins which contain sugar residues to generate dialdehydes which in turn cross-link with each other. Similar results can be obtained by employing a carbodiimide reagent to activate endogenous carboxylate functions of the protein molecules which then react with amino functions of other protein molecules to effect cross-linking by formation of amide linkages.

The desired cross-linking can also be achieved by mixing with the antiserum or with the mixture of binding protein and gamma globulin, a difunctional reagent capable of forming covalent bonds with proteins as described, for example, by Wold, Methods Enzymol., Vol. 11, page 617 (1967) and by Means et al., Chemical Modification of Proteins, Holden-Day, Inc., San Francisco, Calif. (1971). The difunctional reagents which are useful usually contain functional groups which react with amino functions such as those that occur in lysine or other amino acid residues of proteins. The difunctional reagents which can be used include those having the general structure Y-B-Z where B may be any aliphatic or aromatic hydrocarbon residue of sufficient length to permit efficient interaction to take place with two or more binding proteins or immunoglobulins, and where Y and Z may be

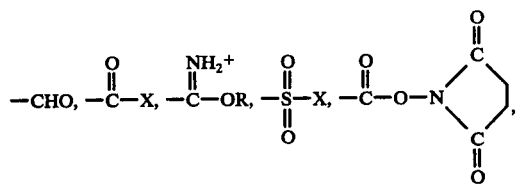

—CH$_2$X, or —N=C=O where X is halogen, preferably bromine or iodine, and where Y and Z may be any compatible pair of different groups or may be identical. The hydrocarbon residue may contain other functional groups to provide such desirable properties such as water-solubility or selective cleavability. Other difunctional reagents which may be used for cross-linking include the bis-diazotized aromatic amines which react with amino acids in proteins containing aromatic rings, and there may also be used dithiols which can undergo disulfide interchange with the disulfide bridges present in the proteins without disrupting the binding site of the binding protein or gamma globulin, and anhydrides of dicarboxylic acids such as adipic anhydride which react with amino groups. The difunctional reagents of choice for the purpose of the present invention are alkyl dialdehydes, such as the dialdehyde made by reacting cyclohexanediol-1,2 with sodium periodate; glutaraldehyde is particularly preferred, optimum results being obtained when the glutaraldehyde is present at a concentration of 0.001 to 0.1 molar in the antiserum or mixture of binding protein and gamma globulin to be cross-linked.

The desired cross-linking can be carried out in a glass or other container, after which the cross-linked antiserum or cross-linked mixture of binding protein and gamma globulin can be brought into contact with the surface of the solid polymeric material, or, as pointed out above, the cross-linking may be carried out in contact with the polymeric material at a pH below 8, after which the pH is raised to 8–10 to cause adsorption on the polymer surface to occur. There may be used as the polymeric material any of those materials described in Catt U.S. Pat. No. 3,646,346, the polymeric material preferably being in the form of a test tube or similar container made of such conventional polymeric materials as polystyrene, polyethylene, nitrocellulose, copolymers of acrylonitrile with styrene and the like, polypropylene being preferred.

There may be included in the cross-linked serum or cross-linked mixture of binding protein and gamma globulin additional ingredients which serve to stabilize the coating, including reducing agents such as sodium borohydride or sodium cyanoborohydride to inactivate residual cross-linking agents such as dialdehydes; ascorbic acid or other antioxidants; and sodium azide or other inhibitors of bacterial action.

Adsorption onto the surface of the polymeric material of the cross-linked gamma globulins from the antiserum or of the cross-linked binding protein and gamma globulin from a solution thereof can be accomplished simply by maintaining the antiserum or solution together with a suitable buffer at pH 8–10, in contact with the previously cleaned and dried polymeric surface for a period of time ranging from minutes to many hours at room temperature; elevated temperatures up to 40° C. may be employed but ambient temperature (room temperature) is usually more convenient. After the desired adsorption has occurred to provide a coating of cross-linked gamma globulins or cross-linked binding protein and gamma globulin on the polymeric surface, the coating solution is removed and the surface washed with a buffer to remove any unadsorbed material, after which the coated polymeric material is dried at room temperature. The coated polymeric material is stable during storage in the dry state over a period of many months.

To carry out an immunoassay, the serum sample to be assayed is brought into contact with the coated surface of polymeric material by placing the sample, for example, within a coated plastic test tube along with a known amount of labeled antigen in buffer. Competition between unlabeled antigen in the sample and the labeled antigen determine the amount of activity which is bound to the coating of the tube. After completion of the binding reaction, the liquid phase, which contains the unbound antigen, both labeled and unlabeled, is removed from the tube, after which the amount of labeled antigen which is bound can be determined in the usual manner and compared with a standard. When the antigen is labeled with a radioactive atom, conventional counters can be used to determine the amount of radiation emitted by the tube. When the antigen is labeled with an enzyme as described, for example, by Avrameas, Immunochemistry, Vol. 6, pages 43–52 (Pergamon Press, 1969), the amount of labeled antigen can be determined by measuring enzymatic activity of the tube. When the antigen is labeled with a fluorophore, for example by reacting the antigen with anthroyl carboxylic acid or with 1-dimethylaminonaphthalene-5-sulfonic acid or with a fluorescein derivative, e.g., fluorescein isothiocyanate, the amount of labeled antigen can be determined by measuring fluorescence as described by Dandliker et al., Immunochemistry, Vol. 10, 219 (1973) or by Aalberse, Clin. Chim. Acta, Vol. 48, 109 (1973). However, the labeling is accomplished, the labeled material serves as a tracer.

The following specific examples are intended to illustrate more fully the nature of the present invention without serving as a limitation upon its scope.

EXAMPLE 1

The gamma globulin fraction of a rabbit antiserum to thyroxine (tetraiodothyronine, T4) is isolated by treating one ml. of the serum for 18 hours at 4° C. with an equal volume of 80% saturated ammonium sulfate, pH 7.1. The precipitated gamma globulin fraction is spun down in a refrigerated centrifuge at 3000 rpm. for 30 minutes, then diluted in 2000 ml. of an isotonic 0.01M phosphate buffer pH 6.0. To this is added 400 ml. of 0.02M glutaraldehyde cross-linking reagent in distilled water. This mixture is allowed to react for 20 minutes at 37° C. and is then diluted for coating by the addition of 2000 ml. of 1M phosphate buffer pH 8.5., to give a final dilution of cross-linked gamma globulin of 1/4400. One ml. aliquots of this coating solution are introduced into the bottom of clean, dry polypropylene plastic tubes. After incubation for 1 hour at 37° C., the tubes are aspirated and washed twice with an isotonic 0.01M tris buffer pH 7.4 containing 0.1% gelatin to remove any unadsorbed cross-linked gamma globulin. The tubes are dried at ambient temperature (22°-25° C.) and stored in sealed plastic bags.

A series of assays was run in these coated tubes using 1 ml. of an isotonic 0.01M tris buffer pH 7.4 containing 0.1% gelatin, quantities of inhibitor T4 ranging from 41 pg to 10 ng per tube and 14,000 cpm of $^{125}$I labeled T4 as radiolabeled tracer followed by room temperature incubation for 3 hours. At the minimum quantity of added T4, 59% of the added tracer was bound to the coated tube, decreasing amounts of tracer being bound at higher levels of added T4 as shown in the drawing.

Analysis of the data by a modification of the procedure of Pinckard et al., Handbook of Experimental Immunology, page 498 (Great Britain 1967) gives an apparent affinity constant (K) of $4.5 \times 10^9 M^{-1}$ and the amount of T4 antibody bound to the tube $(Ab_o)$ of $1.8 \times 10^{-10}M$.

When the cross-linking reagent is omitted, the precipitated gamma globulin fraction being simply diluted 1/1000 in a buffer 0.01M in tris, 0.01M sodium chloride and 0.01M sodium azide, pH 8.5, and the diluted gamma globulin (one ml. aliquot) is incubated for 1 hour at 37° C. in polypropylene tubes, then washed as described above to remove unadsorbed gamma globulin, the coated tubes display much lower immunoactivity when tested in the same way by a series of assays under the same conditions as described above. Only 34% of the added tracer is bound at the minimum quantity of added tracer, as shown in FIG. 1, and the displacement curve has a lower slope; the apparent affinity (K) of the coated tube was calculated as $1.9 \times 10^9 M^{-1}$ and the amount of immobilized T4 antibody $(Ab_o)$ as $1.4 \times 10^{-10}M$.

These results show that cross-linking produces approximately the same amount of T4 antibody as does the untreated gamma globulin fraction when the latter is at more than four times the concentration, with maximum binding approaching twice that of the untreated gamma globulin fraction.

EXAMPLE 2

One ml. of a rabbit anti-Angiotensin I-serum (previously shown not to be useful in the Catt procedure) is treated for 18 hours at 4° C. with an equal volume of 80% saturated ammonium sulfate, pH 7.1. The precipitated gamma globulin fraction is spun down in a refrigerated centrifuge at 3000 rpm for 30 minutes and redissolved in 250 ml. of an isotonic 0.01M phosphate buffer, pH 6.0. To the diluted gamma globulin preparation is added 50 ml. of 0.1M glutaraldehyde in distilled water, prepared by weighing out 2 gms of commercial 25% glutaraldehyde and diluting to 50 ml.

The mixture is incubated for 20 minutes at 37° C. with occasional stirring. After the incubation, an additional 250 ml. of isotonic 0.01M phosphate buffer pH 6.0 and 500 ml. of a 0.8M phosphate buffer pH 8.5 are added to raise the pH for efficient coating and to dilute the cross-linked gamma globulin for proper coating. One ml. portions of the coating solution are carefully put into clean, dry polypropylene plastic tubes and allowed to stand undisturbed for 18 hours at ambient temperature, 22°-25° C., after which the coating solution is removed by aspiration and the tube is given two washes with an isotonic 0.01M tris buffer pH 7.4 containing 0.1% gelatin and 0.01M sodium azide. The tubes are dried at the same ambient temperature as above and stored in plastic bags.

The angiotensin I antibody coated tubes prepared by this invention can be used in a radioimmunoassay for angiotensin I according to the following procedure. One ml. of a 0.1M tris buffer adjusted to pH 7.4 with glacial acetic acid is added to the coated tube. One hundred $\mu$l of patient plasma to be assayed is added, as well as 20,000 counts per minute of angiotensin I-5-(3-$^{125}$I tyrosine). The reaction mixture is incubated at ambient temperature (22°-25° C.) with occasional shaking for 3 hours, when the reaction is terminated by aspirating the liquid phase. Separation of bound and free tracer is accomplished by this aspiration. Competition between unlabeled hormone in the patient plasma and the $^{125}$I labeled hormone determines the amount of labeled material bound to the immobilized angiotensin I antibody.

The total immunoactivity of the coated tube can be determined by following the foregoing procedure for radioimmunoassay but omitting the patient plasma. Samples of the coated tubes prepared as described in this example are found by this procedure to bind from 30% to 60% of the amount of the added radiolabeled angiotensin I. In contrast, when the glutaraldehyde cross-linking agent is omitted, being replaced by an equal volume of phosphate buffer, the procedure of this example produces a coated tube having a total immunoactivity less than 10% of the added radiolabeled angiotensin I, an amount so low that the coated tube could not be used for quantitative immunoassay procedures. On the other hand, pretreating the plastic tubes with glutaraldehyde, followed by introducing uncross-linked samples of angiotensin I antibody at the same 1/1000 dilution as above resulted in tubes which bound only 20% of the added radiolabeled angiotensin I.

EXAMPLE 3

One ml. of a rabbit anti-Angiotensin I serum is treated for 18 hours at 4° C. with an equal volume of 80% saturated ammonium sulfate, pH 7.1. The precipitate is spun down in a refrigerated centrifuge for 30 minutes at 3000 rpm and redissolved in 100 ml. of an isotonic 0.01M triethylamine buffer pH 8.5. To this solution is added 100 ml. of 0.0625M dimethyl suberimidate cross-linking reagent in the same buffer and the reaction mixture is incubated for one hour at 37° C. Dilution of the reaction mixture with 800 ml. of 0.01M sodium phosphate, 0.01M sodium azide buffer, pH 9.0, yields one liter of coating solution.

One ml. aliquots of the coating solution are carefully introduced into clean, dry polypropylene plastic tubes and allowed to stand undisturbed for 18 hours at ambient temperature (22°-25° C.). Aspiration of the coating solution terminates the coating process. After washing, as previously described, the tubes are dried and stored in sealed plastic bags at room temperature.

Comparison of these coated tubes with tubes coated with angiotensin 1 antibody without cross-linking using the radioimmunoassay procedure of Example 1 (except that a dilution of 1/1000 was used for both cross-linked and uncross-linked angiotensin I antibody) yields values of $K = 2 \times 10^8 M^{-1}$ and $Ab_0 = 1.3 \times 10^{-9}M$ for cross-linked angiotensin I antibody and $K = 1.5 \times 10^8 M^{-1}$, $Ab_0 = 4.1 \times 10^{-10}M$ for uncross-linked angiotensin I antibody. In the case of the cross-linked antibody, from 30% to 60% of the radiolabeled tracer is bound at minimal addition of unlabeled hormone, but only 10–15% in the case of the uncross-linked angiotensin I antibody under the same conditions.

EXAMPLE 4

Hog gastric intrinsic factor is a binding protein for vitamin B-12 which, unlike rabbit gamma globulin, apparently does not adsorb to plastic surfaces in amounts sufficient to prepare a useful solid phase immobilized adsorbent. Hovver, it is possible to prepare a solid phase immobilized vitamin B-12 adsorbent by using rabbit gamma globulin covalently bound to the binding protein. The modified gamma globulin will adsorb to plastic and carry with it the binding protein.

Five hundred microliters of an isotonic 0.01M phosphate buffer, pH 6.0, containing rabbit gamma globulin at a dilution of 1:200 and 100 μg of intrinsic factor is introduced into the bottom of a clean, dry polypropylene plastic tube. To this is added 100 μl of 0.2M glutaraldehyde in distilled water. This mixture is allowed to react for 10 minutes at room temperature. Five hundred microliters of a 1M pH 8.5 phosphate buffer is added to raise the pH for more efficient coating. The tube is then coated for 1 hour at 37° C., aspirated and washed twice with an isotonic 0.01M tris buffer pH 7.4 containing 0.1% gelatin to remove unadsorbed binding protein-antibody conjugate. After drying at ambient temperature the tubes are stored in sealed plastic bags. In this example, cross-linking and coating are carried out in the same tube.

One ml. of a glutamic acid-potassium cyanide-gelatin buffer containing 5400 cpm of $^{57}Co$ labeled vitamin B-12 tracer is incubated in the binding protein-gamma globulin conjugate coated tube, prepared as described above, at 4° C. for 18 hours. On aspiration, it is found that 32% of the added labeled tracer is bound to the tube. Deletion of any one of the three critical components in the coating solution, i.e., glutaraldehyde, intrinsic factor and rabbit gamma globulin results in tubes that bind indistinguishably from background, or about 2% of added tracer.

EXAMPLE 5

A 5 μl aliquot of an antiserum to Vitamin B-12 is dissolved in 0.5 ml. of 0.1M pH 6.0 potassium phosphate buffer. To this is added 0.5 ml. of a 0.4M solution of 1-cyclohexyl-3-(2-morpholinoethyl)-carbodiimide metho-p-toluenesulfonate in the same buffer. The reaction mixture is incubated for one hour at 37° C. to allow activation of endogeneous carboxylate functions and their subsequent reaction with amino function to give cross-linking via intermolecular amide bonds.

This reaction mixture is then diluted in an isotonic phosphate buffer, pH 9.5, such that the original antiserum is at a dilution of 1/5000. One ml. aliquots of this solution are introduced into clean dry polypropylene tubes and allowed to stand for 18 hours at ambient temperature (22°–25° C.) to allow the polymerized gamma globulin to coat the surface of the tube. After coating, the tubes are aspirated and washed with a 0.1% gelatin solution in isotonic 0.01M tris buffer pH 7.4 to remove unadsorbed cross-linked gamma globulin.

When tubes coated in this maner are assayed with 10,000 cpm of $^{57}Co$ labeled vitamin B-12 tracer for 30 minutes at 37° C., 26% of the added tracer is bound. If tubes are coated with the same antiserum that has not been treated with carbodiimide, only 18% of the added tracer is bound. Thus, the cross-linking of the gamma globulin solution with carbodiimide increases binding by 44%.

EXAMPLE 6

Ten mls. of a 1/100 dilution in isotonic saline of an ammonium sulfate fractionated digitoxin antiserum adjusted to pH 9.0 with sodium carbonate is treated with 21.4 mg. of sodium periodate. The cleavage of 1,2-diol functions of the sugar residues of the gamma globulin molecules to form aldehydes and their subsequent reaction with the amino functions of other gamma globulin molecules occurs at ambient temperature (22°–25° C.) in 12-18 hours, leading to cross-linked gamma globulins. After a 90-fold dilution in 0.01M tris buffer, containing 0.01M sodium chloride and 0.01M sodium azide at pH 8.5, one ml. aliquots of the 1/9000 diluted cross-linked gamma globulin are introduced into clean dry polypropylene tubes and allowed to coat for 15 minutes at 37° C. After coating the tubes are aspirated and washed with a 0.1% gelatin in isotonic 0.01M tris buffer pH 7.4 to remove unadsorbed cross-linked gamma globulin.

When tubes prepared in the above manner are assayed with 11,000 cpm of $^{125}I$ digitoxigenin derivative tracer in 1.0 ml. of tris buffer for 45 minutes at 37° C., 35.2% of the added tracer is bound to the solid phase immobilized cross-linked gamma globulin. If the same ammonium sulfate fractionated antiserum, without treating with sodium periodate, is used to coat tubes at a dilution of 1/9000 under identical conditions, only 12.4% of the added counts are bound in 45 minutes at 37° C. Thus, cross-linking the gamma globulins with sodium periodate allows one to produce tubes that bind 300% more tracer than tubes coated with native gamma globulin at the same dilution.

EXAMPLE 7

An aliquot of an ammonium sulfate fractionated digitoxin antiserum is diluted 1/50 in isotonic 0.01M phosphate buffer pH 7.4 and heated in a glass vial at 75° C. for 5–20 minutes. After heating, the solution is diluted 80-fold in a 0.01M tris, 0.01M sodium chloride, 0.01M sodium azide pH 8.5 buffer, and one ml. aliquots are introduced into clean dry polypropylene tubes for 15 minutes at 37° C. After this incubation, the tubes are aspirated and washed with a 0.1% gelatin in isotonic 0.01M tris buffer pH 7.4.

When these tubes were assayed with 11,000 cpm of an $^{125}I$ digitoxigenin derivative tracer in 1.0 ml. of an isotonic 0.01M tris pH 7.4 buffer, 42–45% of added tracer was found to be bound to the solid phase immobilized cross-linked digitoxin antibody on separation of bound and free by aspiration of the free tracer. If the same fractionated digitoxin antiserum is not heat treated, but otherwise handled in an identical manner, only 34% of added counts are bound to tubes coated with this antiserum. Thus, heat treatment increased binding by about 30%.

What is claimed is:

1. A method of making a solid immunoadsorbent for use in immunoassay procedures which comprises cross-linking the gamma globulin content of low titer antiserum, and bringing the cross-linked gamma globulin at pH 8 to 10 into contact with a surface of a solid polymeric material capable of adsorbing gamma globulin to form a coating of cross-linked gamma globulin adsorbed on said surface.

2. A method as claimed in claim 1 in which the cross-linking is carried out by adding to the gamma globulin a difunctional reagent capable of forming covalent bonds with proteins.

3. A method as claimed in claim 2 in which the reagent is glutaraldehyde.

4. A method as claimed in claim 2 in which the reagent is dimethyl suberimidate.

5. A method as claimed in claim 2 in which the reagent is a carbodiimide.

6. A method as claimed in claim 2 in which the reagent is sodium periodate.

7. A method as claimed in claim 1 in which the cross-linking is carried out by heating the gamma globulin.

8. A method as claimed in claim 1 in which the polymeric material is polypropylene.

9. A method of making a solid immunoadsorbent for use in immunoassay procedures which comprises cross-linking a binding protein with gamma globulin to form a cross-linked material, and bringing the cross-linked material at pH 8 to 10 into contact with a surface of a solid polymeric material capable of adsorbing gamma globulin to form a coating of cross-linked material adsorbed on said surface.

10. A method as claimed in claim 9 in which the cross-linking is carried out by mixing said binding protein and gamma globulin with a difunctional reagent capable of forming covalent bonds with proteins.

11. A method as claimed in claim 10 in which the reagent is glutaraldehyde.

12. A method as claimed in claim 11 in which the reagent is dimethyl suberimidate.

13. A method as claimed in claim 9 in which the cross-linking is carried out by mixing said binding protein and gamma globulin with a carbodiimide.

14. A method as claimed in claim 13 in which the cross-linking is carried out by mixing said binding protein and gamma globulin with sodium periodate.

15. A method as claimed in claim 9 in which the cross-linking is carried out by heating a mixture of said binding protein and gamma globulin.

16. A method as claimed in claim 9 in which the polymeric material is polypropylene.

17. In a kit for determination of proteins, drugs, steroid hormones and other physiologically active materials in aqueous samples comprising a test tube having an inner surface of solid polymeric material capable of adsorbing gamma globulin and a supply of labeled tracer, the improvement comprising a coating on said surface selected from the group consisting of cross-linked gamma globulin and binding protein cross-linked to gamma globulin.

18. A kit as claimed in claim 17 in which the polymeric material is polypropylene.

19. A kit as claimed in claim 18 in which the tracer is radioactively labeled antigen.

20. A kit as claimed in claim 18 in which the tracer is enzyme labeled antigen.

21. A kit as claimed in claim 18 in which the tracer is fluorophore labeled antigen.

* * * * *